(12) United States Patent
Taft

(10) Patent No.: US 10,382,025 B2
(45) Date of Patent: Aug. 13, 2019

(54) CIRCUIT FOR MEETING SETUP AND HOLD TIMES OF A CONTROL SIGNAL WITH RESPECT TO A CLOCK

(71) Applicant: TEXAS INSTRUMENTS INCORPORATED, Dallas, TX (US)

(72) Inventor: Robert Callaghan Taft, Munich (DE)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 15/933,021

(22) Filed: Mar. 22, 2018

(65) Prior Publication Data
US 2018/0302067 A1   Oct. 18, 2018

Related U.S. Application Data

(60) Provisional application No. 62/485,315, filed on Apr. 13, 2017.

(51) Int. Cl.
| | |
|---|---|
| *H03K 5/01* | (2006.01) |
| *H03K 3/037* | (2006.01) |
| *G06F 1/12* | (2006.01) |
| *H03K 19/21* | (2006.01) |
| *H03K 5/15* | (2006.01) |
| *H03K 5/00* | (2006.01) |

(52) U.S. Cl.
CPC ............... *H03K 5/01* (2013.01); *G06F 1/12* (2013.01); *H03K 3/037* (2013.01); *H03K 3/0375* (2013.01); *H03K 5/15046* (2013.01); *H03K 5/15066* (2013.01); *H03K 19/21* (2013.01); *H03K 2005/00078* (2013.01)

(58) Field of Classification Search
CPC ........ H03K 5/01; H03K 3/037; H03K 3/0375; H03K 5/15046; H03K 5/15066; H03K 19/21; H03K 2005/00078; G06F 1/12
See application file for complete search history.

(56) References Cited

U.S. PATENT DOCUMENTS

| | | | |
|---|---|---|---|
| 6,731,667 B1 | 5/2004 | Lee et al. | |
| 7,772,889 B2 | 8/2010 | Naffziger | |
| 2008/0301485 A1* | 12/2008 | Rombach | G11C 7/04 |
| | | | 713/600 |
| 2008/0313485 A1 | 12/2008 | Frank et al. | |
| 2009/0256593 A1 | 10/2009 | Naffziger | |

OTHER PUBLICATIONS

International Search Report in corresponding PCT Application No. PCT/US2018/027603, dated Oct. 18, 2018 (2 pages).

* cited by examiner

*Primary Examiner* — Daniel C Puentes
(74) *Attorney, Agent, or Firm* — John R. Pessetto; Charles A. Brill; Frank D. Cimino

(57) ABSTRACT

A circuit includes a plurality of series-coupled delay buffers and a plurality of logic gates. Each logic gate includes first and second inputs. The first input of each logic gate is coupled to a corresponding one of the delay buffers. The circuit also includes a plurality of flip-flops. Each flip-flop includes a data input and a data output. The data input is coupled to an output of a corresponding one of the logic gates and the data output is coupled to the second input of one of the corresponding logic gates.

13 Claims, 5 Drawing Sheets

CIRCUIT FOR MEETING SETUP AND HOLD TIMES OF A CONTROL SIGNAL WITH RESPECT TO A CLOCK

RELATED APPLICATIONS

This application claims priority to U.S. Provisional Application No. 62/485,315, filed Apr. 13, 2017, which is hereby incorporated by reference.

BACKGROUND

The output of flip-flops and other types of docked synchronous components change state responsive to the active edge of a clock. Compliance of setup and hold times relative to the dock edges permits the flip-flops' output to correctly change state. The setup time is the amount of time that the input data signal must be at its correct logic level before the active edge of the clock. The hold time is the amount of time that the input data must remain at its correct logic level after the active edge of the dock, Within a given clock signal cycle, the input data must remain stable during both the setup and hold times and thus the input data can only change state during that portion of the clock signal that is outside the setup and hold time periods. As clock frequencies increase and thus the period of each clock signal decreases, the setup and hold times represent a larger portion of the clock cycle which means that less time is available in each clock cycle during which the input data is permitted to change state without violating the setup and hold timing requirements.

SUMMARY

In one example, a circuit includes a plurality of series-coupled delay buffers and a plurality of logic gates. Each logic gate includes first and second inputs. The first input of each logic gate is coupled to a corresponding one of the delay buffers. The circuit also includes a plurality of flip-flops. Each flip-flop includes a data input and a data output. The data input is coupled to an output of a corresponding one of the logic gates and the data output is coupled to the second input of one of the corresponding logic gates.

In another example, a circuit includes a plurality of series-coupled delay buffers and a plurality of logic gates. Each logic gate includes first and second inputs. The first input of each logic gate is coupled to a corresponding one of the delay buffers. The circuit also includes a first plurality of flip-flops and a second plurality of flip-flops. Each of the first plurality of flip-flops includes a first data input and a first data output. The first data input is coupled to an output of a corresponding one of the logic gates and the first data output is coupled to the second input of one of the corresponding logic gates. Each of the second plurality of flip-flops includes a second data input and a second data output. The second data input is coupled to the first input of a corresponding one of the plurality of logic gates.

In yet another example, an integrated circuit (IC) includes a delay assessment circuit coupled to receive a clock and a control signal and to generate a plurality of bits indicative of setup and hold timing margins for variable amounts of delay between the clock and the control signal. A first register stores the plurality of bits from the delay assessment circuit. A second register can be programmed to store a programmable delay value. A multiplexer couples to the delay assessment circuit and to the second register. The multiplexer receives a plurality of delayed control signals from the delay assessment circuit and selects one of the plurality of delayed control signals responsive to a selection signal from the second register.

BRIEF DESCRIPTION OF THE DRAWINGS

For a detailed description of various examples, reference will now be made to the accompanying drawings in which.

DETAILED DESCRIPTION

The circuits described herein provide an indication of a successful or unsuccessful latch of an input signal relative to a clock edge for varying degrees of delay introduced into the input signal. Based on the output indication, a suitable value can be determined for the amount of delay of the input signal relative to the clock. The disclosed circuits permit a single read of a register containing the indication from which a suitable delay value can be determined.

Figure 1:
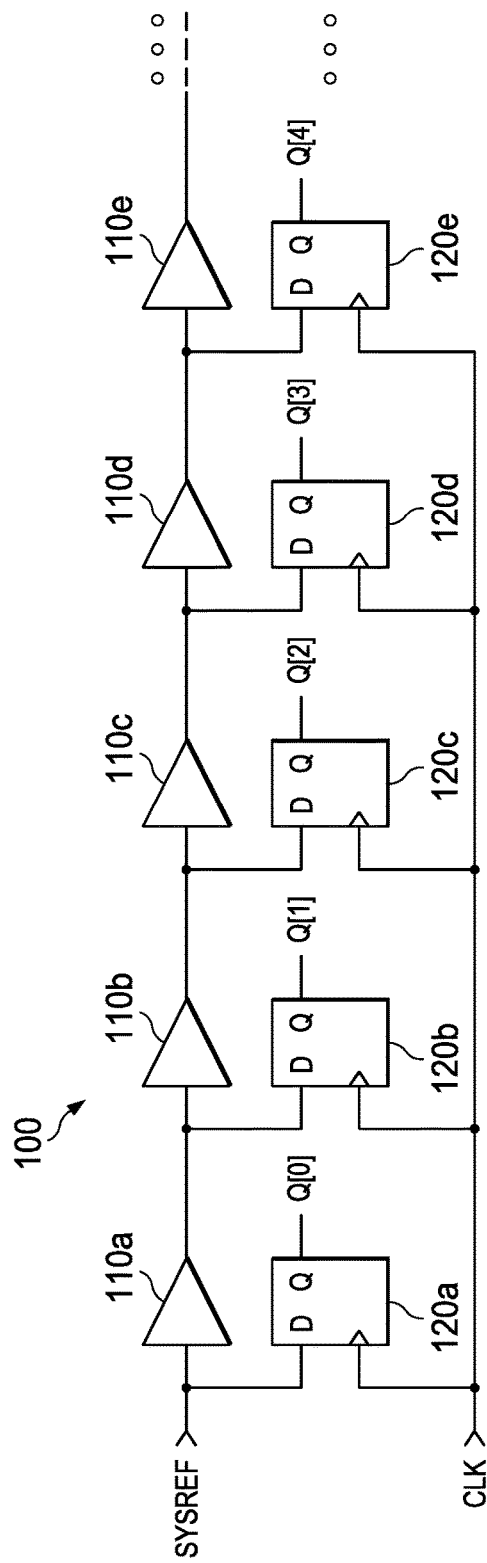
FIG. 1 illustrates an example of a circuit for assessment of a suitable delay between a control signal, labeled SYSREF, and a clock signal.

FIG. 1 shows one example of a delay assessment circuit 100. The delay assessment circuit includes a plurality of series-coupled delay buffers 110*a*, 110*b*, 110*c*, 110*d*, 110*e*, etc. Although five delay buffers 110*a*-110*e* (collectively delay buffers 110) are shown in this example, any number of delay buffers can be included. The delay assessment circuit also includes a plurality of flip-flops 120*a*, 120*b*, 120*c*, 120*d*, 120*e*, etc. Each flip-flop 120*a*-120*e* (collectively flip-flops 120) is a D flip-flop in this example and more or less than the five flip-flops are possible. The delay assessment circuit 100 generally includes one flip-flop 120*a*-120*e* for each corresponding delay buffer 110.

Each delay buffer 110 introduces a fixed amount of time delay between its input and output. A control signal is provided to the input of the first delay buffer 110*a*. The delay buffer can be any passive or active element which passes a signal with a delay. For example, a buffer can be used as a delay buffer, where the buffer can be non-inverting, complementary metal oxide semiconductor (CMOS)-based circuits, current mode logic (CML) devices, etc. The buffer may comprise two stages of an n-type metal oxide semiconductor (NMOS)/p-type metal oxide semiconductor (PMOS) inverter, and may include compensation so that its delay does not vary with changes in temperature or supply. In some cases, the delay buffer has a static delay, while in other cases, the delay buffer may have a configurable delay. The control signal in this example is a system reference (SYSREF) signal which is used to synchronize multiple chips in a system in accordance with the JESD204B standard. In other examples, the control signal can be other than SYSREF. SYSREF is provided to delay buffer 110*a* which produces on its output a delayed version of SYSREF. The delayed SYSREF from delay buffer 110a is provided to an input of the next delay buffer 110b in the series chain of delay buffer and delay buffer 110b adds additional delay to SYSREF. As such, the outputs of the delay buffers 110 provide SYSREF with varying degrees of time delay.

Figure 2:
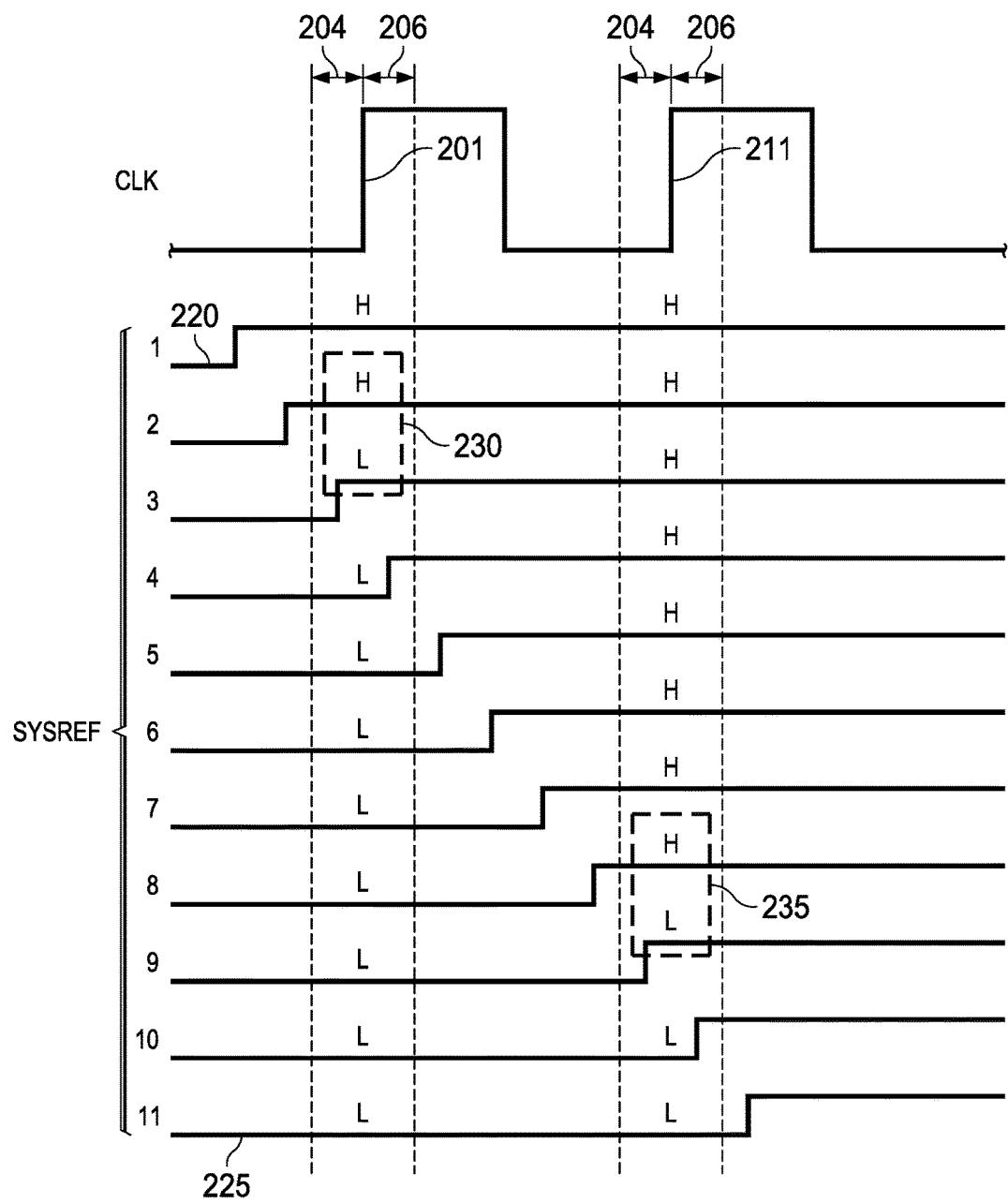
FIG. 2 illustrates data produced by the example circuit of FIG. 1 from which the suitable delay can be determined.

Each flip-flop 120 in this example includes a data input (D) and an output (Q). A clock input of each flip-flop 120 receives a clock signal (CLK). Upon an active edge (assumed to be a rising edge in the disclosed examples) of CLK, each flip-flop 120 latches the logic value present on its D input on to its Q output. FIG. 2 illustrates an example of a timing diagram for the different delayed versions of SYSREF (referred to as "delayed SYSREFs") relative to CLK. Two rising edges 201 and 211 of CLK are shown along with 11 different delayed SYSREFs. The integer delay values 1-11 shown in FIG. 2 refer to the output of 10 daisy-chained delay buffers 110. Delay value 1 in this example represents SYSREF without having passed through any delay buffer as shown in FIG. 1 as the D input to flip-flop 120a. Reference numeral 220 represents SYSREF with the least amount of delay (e.g., SYSREF without passing through any delay buffer 110) and reference numeral 225 represents SYSREF with the largest amount of delay (e.g., delayed SYSREF from the last delay buffer 110 in the series chain of delay buffers 110). In this example, SYSREF is initially low (L) and is asserted high (H) to start a synchronization process in accordance with JESD204B. Due to the various delay buffers 110, the rising edge of SYSREF occurs at different points in time across the various delay buffers. FIG. 2 also shows the setup time 204 and the hold time 206 relative to each clock edge 201, 211.

Relative to clock edge 201, SYSREF with the least amount of delay (delay values 1 and 2) are stable high during the setup and hold times and thus the flip-flops 120a and 120b corresponding to those delay buffers 110a and 110b will latch highs (H) on their outputs as indicated. The next two delayed SYSREFs (corresponding to delay values 3 and 4) have rising edges that occur during the setup or hold times and thus violate the setup and hold timing margins relative to clock edge 201. If the setup or hold timing margin violation is large enough, the flip-flops 120 corresponding to those particular delay buffers will latch lows (L) on their outputs as shown. The remaining delayed SYSREFs (corresponding to delay values 6-11) are stable low during the setup and hold times 204, 206 for clock edge 201 and thus are also latched as lows by their corresponding flip-flops 120. In summary, the first two delayed SYSREFs (those with the least amount of delay) are latched by their flip-flops as H and the remaining delayed SYSREFs are latched as L either because they were not stable high during the entire setup and hold time or because they were stable low during the entire setup and hold time. The latched H and L logic levels are the latched Q outputs of flip-flops 110 and are shown in FIG. 1 as Q[0], Q[1], Q[2], etc.

At the subsequent edge 211 of CLK, delayed SYSREFs corresponding to delay values 1-8 are stable high during the setup and hold times 204, 206 for clock edge 211 and thus are latched as H by their corresponding flip-flops 120. The remaining delayed SYSREFs (delay values 9-11) latch as lows either due to setup and/or hold time violation (which is the case for delay values 9 and 10) or because the delayed SYSREF was stable low during the entire setup and hold time (delay value 11).

Reference numeral 230 in FIG. 2 identifies delayed SYSREFs for delay values 2 and 3. SYSREF with delay value 2 was latched as a logic high (H) because it was stable high during the setup and hold times for clock edge 201. SYSREF with delay value 3 was latched as a logic low (L) because of the aforementioned setup or hold time violation. Similarly, reference numeral 235 identifies a consecutive pair of delayed SYSREFs that also are latched has logic high for one and logic low for the next. This consecutive high/low latching of SYSREF provides an indication that the corresponding amount of delay (delay values 2/3 for clock edge 201 and delay values 8/9 for clock edge 211) is very close to a clock edge. Based on these latched output values from the flip-flops 120, an amount of delay to implement for SYSREF should be somewhere approximately halfway between delay values 2, 3 and delay values 8, 9. A delay value of 6 would be an appropriate choice in this example. By setting the amount of delay for SYSREF to a delay value of 6 (which corresponds to the output of the sixth delay buffer in the series-connected chain of delay buffers; or the output of the fifth delay buffer if delay value 1 corresponds to an un-delayed SYSREF), the rising edge of SYSREF will not occur during the setup and hold time of a rising edge of CLK. As such, there will be no setup or hold timing violation and thus SYSREF will be correctly latched by the chip. As will be explained below, in some examples the Q outputs of the flip-flops 120 are written into a register. The register can then be read for a determination of a suitable amount of SYSREF delay. Once the suitable amount of SYSREF delay is determined, another register can be programmed to cause the output of the flip-flop 120 corresponding to the delay buffer 110 which maps to the determined delay value as the SYSREF signal to be used for synchronization purposes.

Figure 3:
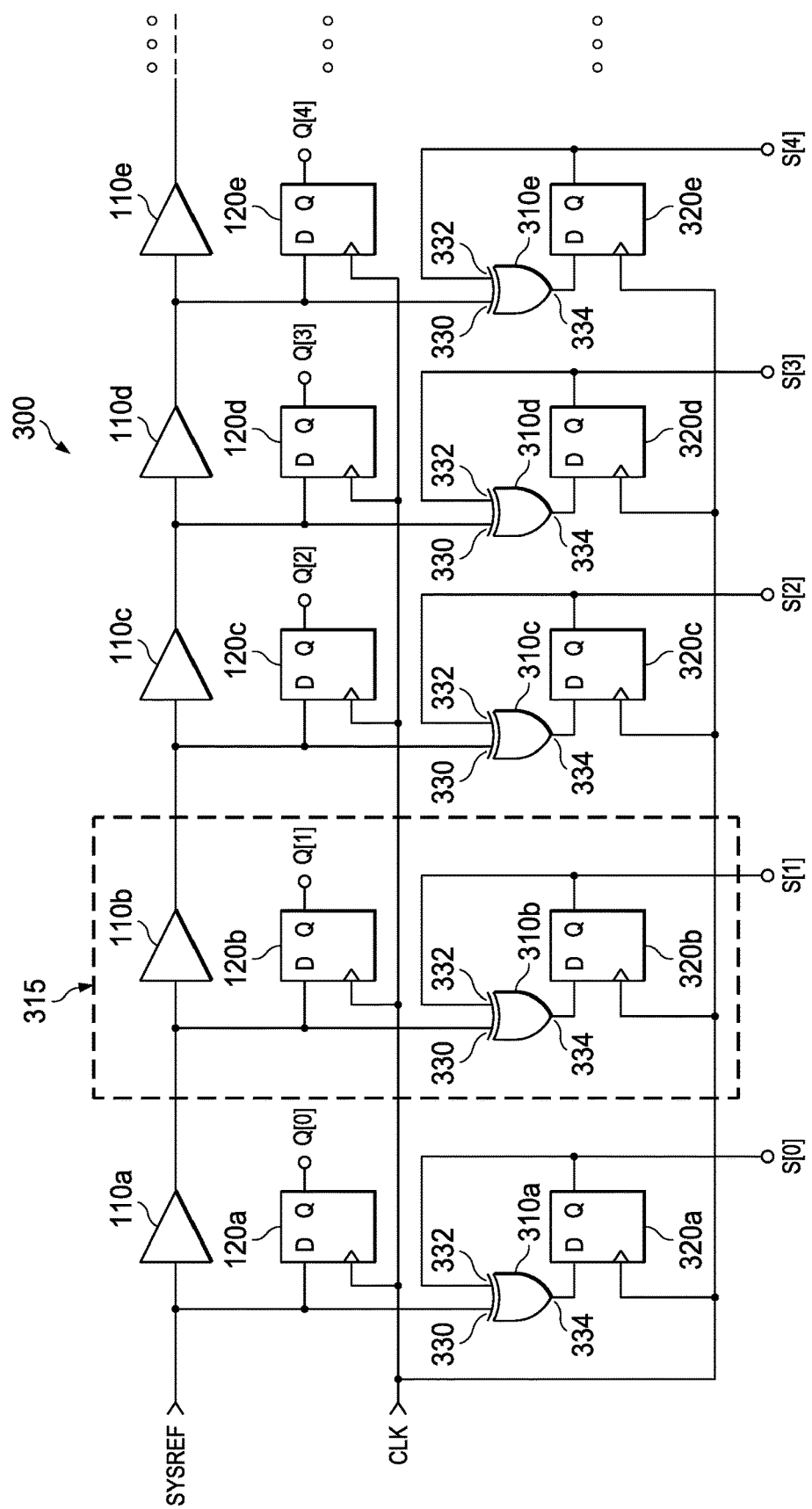
FIG. 3 illustrates another example of a circuit for assessment of a suitable delay between a control signal and a clock signal.

One issue with the example of FIG. 1 is that with each successive rising edge of CLK, the Q outputs of the flip-flops 120 change state thereby losing the previous state. It is desirable to know which flip-flops 120 latch a logic high and which flip-flops 120 latch a logic low upon the first CLK rising edge that occurs when SYSREF becomes high. That set of highs and lows of flip-flops 120, however, are lost upon the next CLK rising edge. FIG. 3 shows an example of a delay assessment circuit 300 which preserves the information indicative of the desired state if the state of the flip-flops cannot otherwise be read before the next CLK rising edge occurs.

The example of FIG. 3 includes the delay buffers 110 and the flip-flops 120 from FIG. 1. A set of logic gates 310 and another set of flip-flops 320 (e.g., D flip flops) are shown. The logic gates 310 comprise logic gate 310a, 310b, 310c, 310d and 310e, etc. and are implemented as exclusive-OR gates in the example shown (and are referred to herein as exclusive-OR gates 310), but can include other types of logic gates as desired. In the example of FIG. 3, all of the flip-flops 120 and 320 are clocked with the same clock signal, CLK. For each delay buffer 110, the circuit includes a corresponding flip-flop 120, exclusive-OR gate 310 and a flip-flop 320 as illustrated by dashed box 315. The flip-flops 320 include flip-flops 320a, 320b, 320c, 320d, 320e, etc. The D input to each flip-flop 120 may be coupled to a delay buffer 110 as shown, or may another delay element (e.g., an XOR gate with one input statically held at a constant level (e.g., 0)) may be included between the delay buffers 110 and the D input of the respective flip-flops 120 to match the delay introduced by logic gates 310.

Each flip-flop 320 includes a data (D) input and a Q output. The Q output of each flip-flop 320 is designated as an S bit (S[0], S[1], S[3], etc.). Each exclusive-OR gate 310 includes two inputs 330 and 332 with input 330 coupled to a corresponding delay buffer 110 and input 332 coupled to the Q output of a corresponding flip-flop 320 as shown. In the example of FIG. 3, each exclusive-OR gate 310 generates a signal on its output 334 that is the exclusive-OR of a corresponding delayed SYSREF and the Q output of the corresponding flip-flop 320. The output 334 from an exclusive-OR gate 320 is provided to the D input of the corresponding flip-flop 320. As such, on each rising CLK edge, flip-flops 320 latch the output of their corresponding exclusive-OR gate 310 as the Q (S[n]) outputs.

An exclusive-OR gate produces an output that is a logic H only if its inputs are of different logic polarity. Thus, each flip-flop 320 will produce an H on its Q output if one of the inputs 330, 332 of the corresponding exclusive-OR gate 310 is a logic H and the other one of the inputs 330, 332 is a logic L; otherwise if both inputs 330 and 332 are logic high or both are logic low, the output of the exclusive-OR gate and thus the latched Q output of the flip-flop will be a logic low.

Initially, all of the flip-flops 320 are cleared so that their Q outputs are logic low. Initially, SYSREF also is logic low. In this state, both inputs to the exclusive-OR gates 310 are low and all of the S[n] bits are low as well. When SYSREF is asserted high, the inputs 330 of one or more (but likely not all) of the exclusive-OR gates 310 will be logic high upon the occurrence of the next rising edge of CLK. For the flip-flops 320 corresponding to those exclusive-OR gates 310 whose input 330 is now logic high, the previous S[n] output (i.e., just before the rising edge of CLK occurred) of those flip-flops is still logic low. Thus, those particular exclusive-OR gates 310 will output a logic high which, upon occurrence of the next edge of CLK will cause the corresponding S[n] bit to be a logic high. For those delay buffers 110 for which the rising edge of SYSREF will not have had time to reach before the CLK edge occurs, those corresponding exclusive-OR gate 310 will have both of their inputs still at a logic low level and thus their corresponding S[n] bits will remain at logic low levels even upon the occurrence of the next edge of CLK. Upon the occurrence of another rising edge of CLK while SYSREF is still asserted high, the output 334 of those exclusive-OR gates 310 that previously had become logic high will now change to logic low because the delayed SYSREF signal input to input 330 of their exclusive-OR gates 310 is a logic high and the previously latched S[n] bit from the corresponding flip-flop 320 was also a logic high. As such, while SYSREF is high, the S[n] bits for those flip-flops for which the rising edge of SYSREF has reached the corresponding delay buffer 110 will toggle between high and low.

Figure 4:
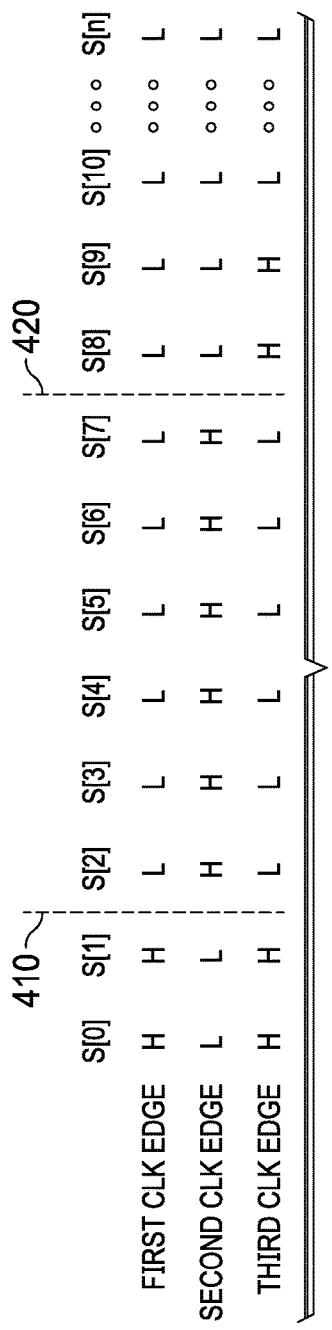
FIG. 4 illustrates data produced by the example circuit of FIG. 3 from which the suitable delay can be determined.

FIG. 4 illustrates an example of the S[n] bits for three consecutive CLK edges. Upon the first occurrence of a CLK edge when SYSREF is high, the first two flip-flops 320a and 320b (corresponding to the least amount of SYSREF delay) latch the logic high SYSREF on their S outputs, while the remaining flip-flops 320 continue to generate logic lows on their outputs as explained above. Thus S[0] and S[1] are logic high and S[2] through S[n] are logic low for the first edge of CLK.

Upon the occurrence of the next (second) edge of CLK, the S[0] and S[1] bits toggle to logic lows due to the logic function of the exclusive-OR gates. Further, S[2] through S[7] become logic high because the rising edge of SYSREF has reached the corresponding delay buffers 110. Bits S[8] through S[n] are still logic low either because the propagating SYSREF rising edge is in violation of the setup and hold margins of the second CLK edge or because SYSREF is still stable low during the setup and hold of the second CLK edge.

Upon occurrence of the third edge of CLK, bits S[0] through S[7] toggle to the opposite polarity states and bits S[8] and S[9] become logic high as SYSREF has finally reached their corresponding delay buffers 110. With each subsequent clock edge (while SYSREF is logic high), the S bits toggle back and forth between H and L. The edges of CLK can be identified in these data. Dashed line 410 identifies the occurrence of the first edge of CLK and dashed line 420 identifies the occurrence of the next edge of CLK. The clock edges are identified by two consecutive S bits being of opposite polarity. The S bits can be captured into a register which can then be read to determine how much delay to use with respect to SYSREF to avoid a setup and hold problem with respect to CLK. A suitable amount of delay corresponds to the delay corresponding to S[4] or S[5] to ensure sufficient margin away from the clock edges 410 and 420.

Figure 5:
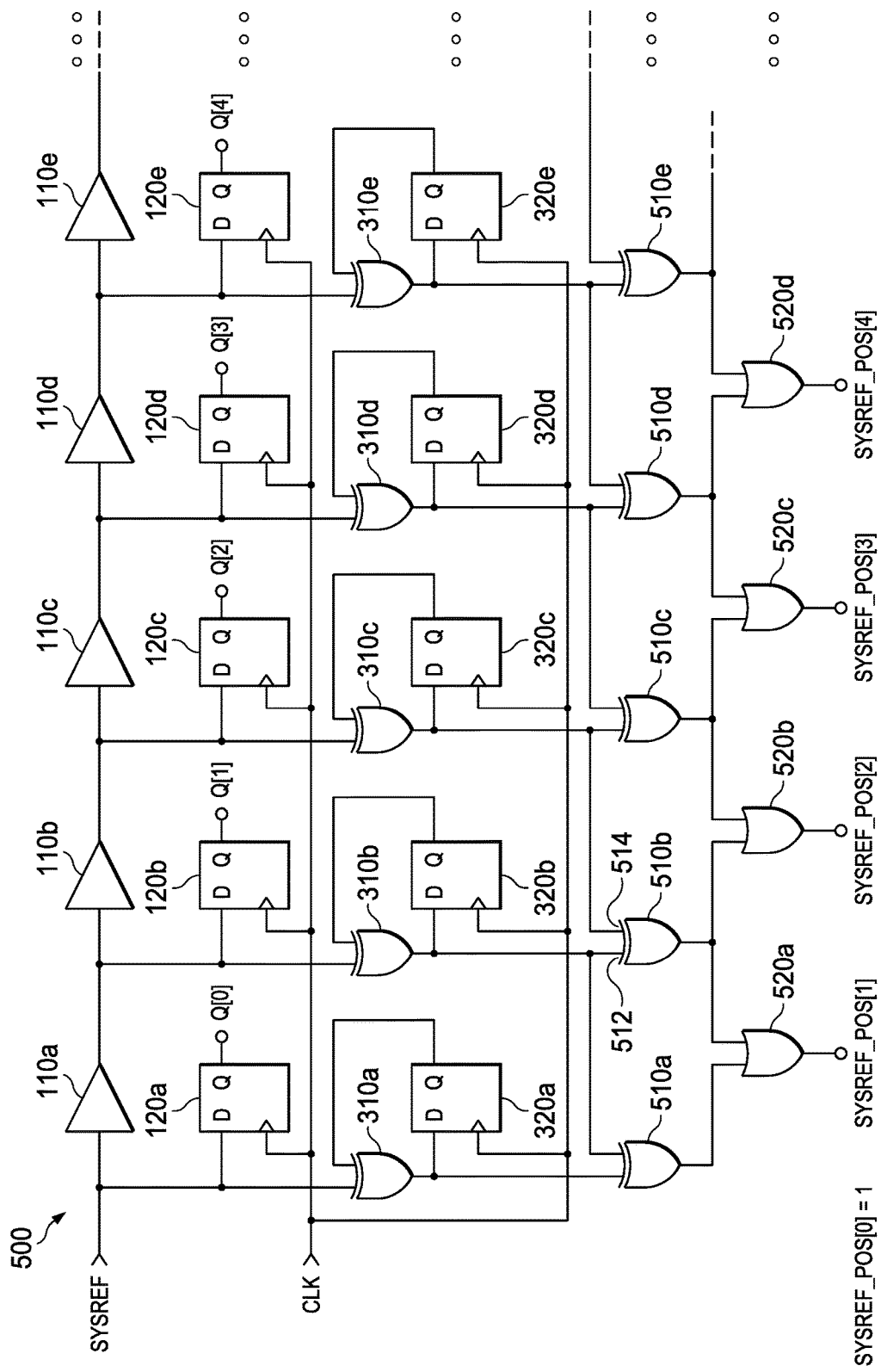
FIG. 5 illustrates another example of a circuit for assessment of a suitable delay between a control signal and a clock signal.
Figure 6:
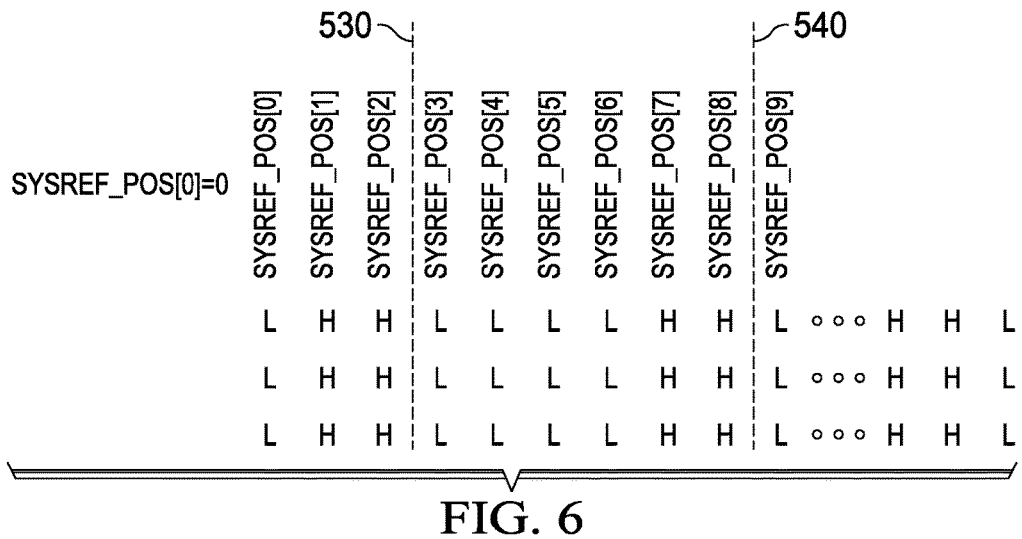
FIG. 6 illustrates data produced by the example circuit of FIG. 5 from which the suitable delay can be determined.

FIG. 5 shows another example of a delay assessment circuit 500. The delay assessment circuit 500 of FIG. 5 is similar to that of FIG. 3 and repeats delay buffers 110, flip-flops 120 and 320 and exclusive-OR gates 310. The example delay assessment circuit 500 of FIG. 5, however, adds another set of logic gates 510a, 510b, 510c, 510d, 510e, etc. which are implemented in this example as exclusive-OR gates (collectively exclusive-OR gates 510) and logic gates 520a, 520b, 520c, 520d, etc. which are implemented in this example as OR gates (collectively OR gates 520). Each exclusive-OR gate 510 includes two inputs 512 and 514 (as illustrated for exclusive-OR gate 510b). Inputs 512 and 514 couple to the outputs of adjacent exclusive-OR gates 310b and 310c. The outputs of adjacent exclusive-OR gates 510 are then OR'd together by an OR gate 510 as shown. Instead of using the Q outputs from flip-flops 320, the outputs of the OR gates 520 are used to identify edges of CLK and are designated as SYSREF_POS[n]. The OR gates 520 produce data similar to that for the example of FIG. 3, but the bits do not toggle between H and L with each successive edge of CLK. FIG. 6 shows the SYSREF_POS[n] bits for three successive edges of CLK. As can be seen, the clock edges are identified by dashed lines 530 and 540, which occur between two SYSREF_POS bits that are of opposite polarity. A suitable amount of delay corresponds to the delay corresponding to SYSREF_POS[5] or SYSREF_POS[6] to ensure sufficient margin away from the clock edges 530 and 540. The least and most significant bits of SYSREF_POS are set at logic highs.

Figure 7:
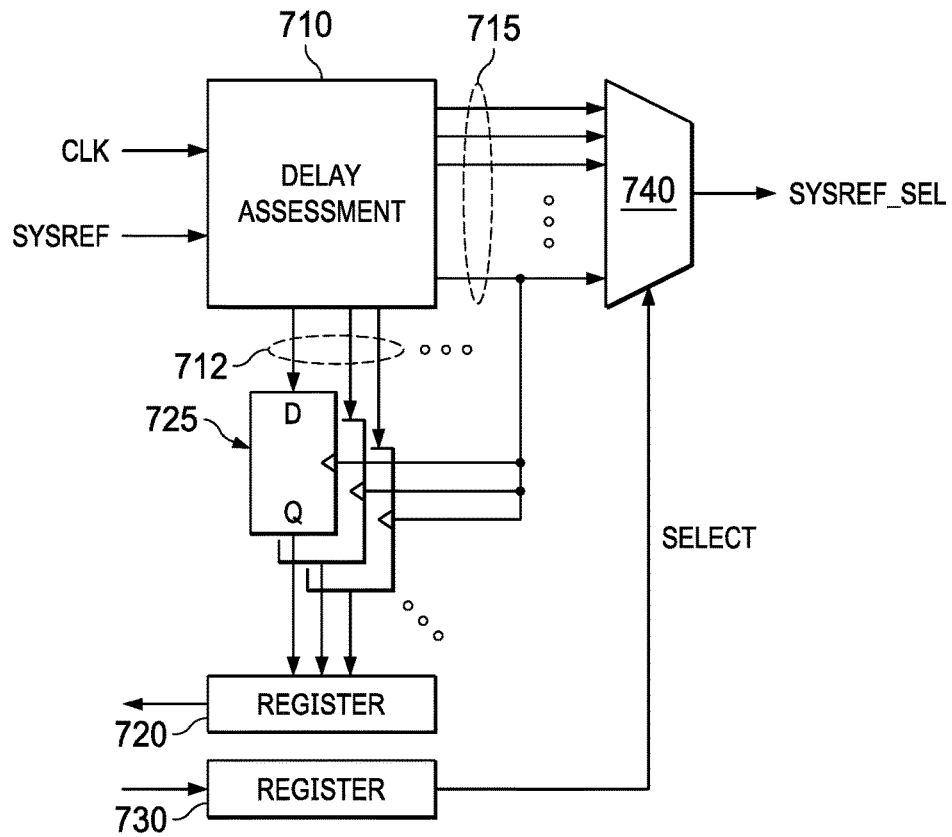
FIG. 7 shows a system using any of the example circuits of FIGS. 1, 3 and 5.

FIG. 7 shows an example of a circuit for the determination and use of the appropriate amount of a delay for SYSREF. The circuit in FIG. 7 may be implemented as an integrated circuit on a common die and includes a delay assessment circuit 710, flip-flops 725, registers 720 and 730 and a multiplexer 740. The delay assessment circuit 710 can be any of the circuits of FIGS. 1, 3, and 5. SYSREF and CLK are provided to the delay determination circuit 710. In the example in which the delay assessment circuit 710 is the circuit of FIG. 5, the output bits 712 are the SYSREF_POS [n] bits and are latched into flip-flops 725 using the most delayed SYSREF signal 715 from the delay assessment circuit 710 (i.e., the output of the flip-flop 120 corresponding to the largest amount of delay). The Q outputs of the flip-flops 725 are then written into register 720. The register 720 can be read by an external electronic device. From the data read from register 720, a determination can be made as to the amount of delay to use for SYSREF as explained above. Once that determination is made, a delay value is programmed into register 730. The interface over which register 720 can be read and register 730 can be written be any suitable interface such as the Serial Peripheral Interface (SPI). The Q outputs of flip-flops 120 are provided as signals 715 to the multiplexer 740 and one of the latched delayed SYSREFs is selected by the multiplexer 740 as the output SYSREF_SEL signal to use by other logic for synchronization purposes. The programmable delay value written to register 730 represents a selection (SELECT) signal to cause the multiplexer 740. The delay assessment circuits described herein are reset (their D flip-flops are cleared) before the next low-to-high transition of SYSREF to be able to correctly capture the next assertion of SYSREF.

Alternatively, if the circuit of FIG. 3 is used as delay assessment circuit 710, output bits 712 are the S[n] bits and bits 715 are the Q output bits of the flip-flops 120. Further, if the circuit of FIG. 1 is used as delay assessment circuit 710, bits 712 and 715 both are the Q[n] bits from flip-flops 120.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A circuit, comprising:
   a plurality of series-coupled delay buffers;
   a plurality of logic gates, each logic gate including first and second inputs, the first input of each logic gate is coupled to a corresponding one of the delay buffers; and
   a plurality of flip-flops, each flip-flop including a data input and a data output, the data input coupled to an output of a corresponding one of the logic gates and the data output coupled to the second input of one of the corresponding logic gates;
   wherein each of the plurality of logic gates includes an exclusive-OR gate.

2. A circuit, comprising:
   a plurality of series-coupled delay buffers;
   a plurality of logic gates, each logic gate including first and second inputs, the first input of each logic gate is coupled to a corresponding one of the delay buffers; and
   a plurality of flip-flops, each flip-flop including a data input and a data output, the data input coupled to an output of a corresponding one of the logic gates and the data output coupled to the second input of one of the corresponding logic gates;
   wherein the plurality of logic gates is a first plurality of logic gates, and the circuit further includes a second plurality of logic gates, each of the second plurality of logic gates including third and fourth inputs, the third input of each of the second plurality of logic gates is coupled to the data input of a corresponding flip-flop and an output of a corresponding one of the first plurality of logic gates, and the fourth input is coupled to the data input of another one of the plurality of flip-flops.

3. The circuit of claim 2, wherein:
   each of the first plurality of logic gates is an exclusive-OR gate;
   each of the second plurality of logic gates is an exclusive-OR gate; and
   each of the plurality of flip-flops is a D flip-flop.

4. The circuit of claim 2, wherein the plurality of flip-flops is a first plurality of flip-flops, and wherein the circuit further comprises:
   a second plurality of flip-flops, each of the second plurality of flip-flops includes a data input and a data output, the data input of each of the second plurality of flip-flops is coupled to a corresponding one of the delay buffers and to the first input of one of the first plurality of logic gates; and
   a multiplexer including a plurality of inputs, wherein each multiplexer input is coupled to a corresponding data output of each of the second plurality of flip-flops.

5. The circuit of claim 4, further comprising:
   a first register to store an output bit from each of the second plurality of logic gates; and
   a second register coupled to a receive a programmed value;
   a control signal derived from the second register's programmed value to control the multiplexer to select a signal on one of the multiplexer's inputs as an output of the multiplexer.

6. A circuit, comprising:
   a plurality of series-coupled delay buffers;
   a plurality of logic gates, each logic gate including first and second inputs, the first input of each logic gate is coupled to a corresponding one of the delay buffers;
   a first plurality of flip-flops, each of the first plurality of flip-flops including a first data input and a first data output, the first data input coupled to an output of a corresponding one of the logic gates and the first data output coupled to the second input of one of the corresponding logic gates; and
   a second plurality of flip-flops, each of the second plurality of flip-flops including a second data input and a second data output, the second data input coupled to the first input of a corresponding one of the plurality of logic gates.

7. The circuit of claim 6, wherein each of the first and second pluralities of flip-flops includes a clock input coupled to receive a common clock signal.

8. The circuit of claim 6, each of the first and second pluralities of flip-flops are D flip-flops.

9. The circuit of claim 6, wherein each of the plurality of logic gates is an exclusive-OR gate.

10. The circuit of claim 6, wherein the plurality of logic gates is a first plurality of logic gates, and the circuit further includes a second plurality of logic gates, each of the second plurality of logic gates including third and fourth inputs, the third input of each of the second plurality of logic gates is coupled to the data input of a corresponding one of the first plurality of flip-flops and an output of a corresponding one of the first plurality of logic gates, and the fourth input is coupled to the data input of another one of the first plurality of flip-flops.

11. The circuit of claim 10, wherein:
   each of the first plurality of logic gates is an exclusive-OR gate;
   each of the second plurality of logic gates is an exclusive-OR gate;
   each of the plurality of flip-flops is a D flip-flop; and
   each of the plurality of flip-flops is a D flip-flop.

12. The circuit of claim 10, further comprising:
   a first register to store an output bit from each of the second plurality of logic gates; and
   a second register coupled to a receive a programmed value indicative of a time delay; and
   a multiplexer including a plurality of inputs, wherein the data outputs of the second plurality of flip-flops are coupled to the multiplexer's inputs.

13. The circuit of claim 12, wherein the multiplexer is configured to select a signal on one of the multiplexer's inputs as an output of the multiplexer based on a control signal derived from the second register's programmed value.

* * * * *